United States Patent
Nevel et al.

(10) Patent No.: US 6,307,953 B1
(45) Date of Patent: *Oct. 23, 2001

(54) SYSTEM FOR ELECTRONICALLY EVALUATING YARN OR FABRIC SAMPLES CELL BY CELL

(75) Inventors: Avishai Nevel, Providence; Kendell W. Gordon, Jr., North Kingston, both of RI (US)

(73) Assignee: Lawson-Hemphill, Inc., Pawtucket, RI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/912,327

(22) Filed: Aug. 18, 1997

Related U.S. Application Data (63) Continuation-in-part of application No. 08/603,587, filed on Feb. 21, 1996.

(51) Int. Cl.[7] .................................................. G06K 9/00
(52) U.S. Cl. .......................... 382/111; 356/238.2; 28/227
(58) Field of Search .......................... 382/111; 356/237.1, 356/237.2, 237.3, 237.4, 237.5, 238.1, 238.2, 238.3, 239.1, 239.2, 385, 429; 348/88; 57/264; 700/130, 131, 132, 133, 134, 135, 136, 137, 138, 139

(56) References Cited

U.S. PATENT DOCUMENTS

| | | | | |
|---|---|---|---|---|
| 4,951,223 | * | 8/1990 | Wales et al. | 364/507 |
| 4,954,976 | * | 9/1990 | Noonan | 364/578 |
| 5,113,454 | * | 5/1992 | Marcantonio et al. | 382/27 |
| 5,181,374 | * | 1/1993 | Aeppli | 57/264 |
| 5,301,129 | * | 4/1994 | McKaughan et al. | 364/430 |
| 5,530,551 | * | 6/1996 | Cantrall et al. | 356/394 |
| 5,537,811 | * | 7/1996 | Pidoux et al. | 57/264 |

* cited by examiner

*Primary Examiner*—Samir Ahmed
(74) *Attorney, Agent, or Firm*—Mirick, O'Connell, DeMallie & Lougee, LLP (57) ABSTRACT

A method for electronically evaluating yarn or fabric samples by delineating a given sample into one or more cells and comparing the cells to each other or to one or more reference cells.

24 Claims, 7 Drawing Sheets

SYSTEM FOR ELECTRONICALLY EVALUATING YARN OR FABRIC SAMPLES CELL BY CELL

CROSS-REFERENCE TO RELATED APPLICATION

This is a continuation-in-part of application Ser. No. 08/603,587, filed on Feb. 21, 1996.

FIELD OF INVENTION

This invention relates to a method for electronically evaluating yarn or fabric samples for grading and clearing purposes by delineating a sample into cells and comparing these cells to one another or to a reference cell, and may also include a neural network which simulates human judgment used to grade yarn or fabric.

BACKGROUND OF INVENTION

There are many known methods for evaluating yarn samples. One such method is linear in that it only measures a yarn sample, from one end to another, in minute linear segments which together, in sequential order from the first segment to the last segment, represent the yarn sample. Each segment represents a single length of yarn and is measured for one or more qualities used to grade the yarn. The representation can be displayed to enable a person to visualize the yarn sample, as if wound onto a taper board or reconfigured into a fabric sample, and to manually check for unacceptable patterns and/or flaws that are too close together. The method may also include a means for electronically counting the number of events or flaws along the length of running yarn and dynamically clearing portions of the running yarn to remove some or all of the events as required to achieve a particular grade of yarn.

The current methods are not able to electronically evaluate long lengths of yarn because to do so under the current methods requires more computer memory and processing than economically feasible for yarn evaluators. The current methods require a computer to memorize the data from each measured segment along the length of a yarn sample.

The current methods do not provide a means for electronically delineating a running yarn, an electronically represented yarn wound onto a taper board, or a fabric sample into blocks or cells, which may or may not be adjacent to one another along the yarn sample, rather than consecutive yarn segments.

The current methods to not provide a means for electronically evaluating a yarn sample or fabric for patterns or flaws located in nonlinear proximity to each other when wound onto a taper board or reconfigured into a fabric. In other words, yarns and fabric samples are evaluated by current methods based how many flaws exist within a given length of yarn, rather than how many flaws exist in a quadrant of yarn, which may comprise nonconsecutive lengths of a yarn sample, when reconfigured onto a taper board or into a fabric. To evaluate reconfigured yarn, the current methods require a visual display, either as an electronic representation of a yarn or fabric sample or as an actual yarn sample wound mechanically onto a taper board, and a person to manually evaluate the display.

SUMMARY OF INVENTION

It is therefore an object of this invention to provide a method for electronically evaluating a yarn or fabric sample or representation by delineating the sample into cells and comparing one or more of these cells to each other.

It is a further object of this invention to provide a method for electronically evaluating longer yarn samples than allowed using current methods.

It is a further object of this invention to provide a method for electronically evaluating a yarn or fabric sample by delineating the sample into cells and comparing one or more of these cells to one or more reference cells.

It is therefore a further object of this invention to provide a method for electronically evaluating a yarn or fabric sample for patterns of flaws.

It is a further object of this invention to provide a method for electronically evaluating a yarn or fabric sample for flaws located in nonlinear (random) proximity to each other.

It is a further object of this invention to provide a method for dynamically clearing portions of a running yarn based on electronically evaluated patterns.

It is a further object of this invention to provide a method for dynamically clearing portions of a running yarn based on flaws located in nonlinear proximity to each other.

It is a further object of this invention to provide a method for electronically displaying electronically evaluated yarn samples in which flaws and/or patterns may be displayed using different shades or colors to represent each different threshold or type of event.

This invention results from the realization that evaluation of yarn and fabric samples should include not only measurements of adjacent linear segments of a yarn sample but also a comparison of one or more blocks or cells of a yarn sample when electronically reconfigured onto a taper board or into a fabric sample.

This invention could be used to replace the current subjective and costly manual evaluation of a yarn or fabric sample for the purpose of locating unacceptable patterns or unacceptable flaws located in nonlinear proximity to each other.

This invention features a method for electronically evaluating one or more measured qualities of one or more yarn or fabric samples, comprising the steps of: assigning one or more physical thresholds for each measured yarn or fabric quality; establishing an event when a measured yarn or fabric quality violates the physical threshold; establishing one or more cells, wherein each said cell represents one or more portions of the yarn or fabric sample; sorting the events in each cell into types of events, wherein a type includes both a measured yarn or fabric quality and a physical threshold; counting the number of events of each type which occur within each cell; and comparing the type and number of each type of events in each cell with a reference cell to determine whether the number of events of each type in each cell exceeds a predetermined number of events of the same type of events in the reference cell.

The method may further include dynamically clearing selected portions of a running yarn on-line. The method may further comprise a neural network which simulates human judgment used to manually grade yarn and which may dynamically clear selected portions of a running yarn on-line to upgrade the running yarn and a means for simulating the effect of clearing a selected portion of the yarn sample.

In another embodiment, this invention features a method for electronically evaluating one or more measured qualities of one or more yarn samples, comprising the steps of assigning a physical threshold for each measured yarn quality; establishing an event when the yarn or fabric quality violates the physical threshold; establishing one or more cells, wherein each cell represents one or more portions of the yarn sample; memorizing the location of each event in each cell; comparing the location of events in one or more cells to the location of events in one or more other cells in the yarn or fabric sample to determine whether a pattern of events exists between two or more cells within a yarn or fabric sample.

This embodiment may further comprise the steps of sorting the events in each cell into types of events, wherein type includes both a measured yarn quality and a physical threshold; counting the number of events of each type which occur within each cell; calculating an average number of events per cell for each type; determining if the number of events of each type occurring within each cell exceeds the average number of events per cell for each type; and locating two or more vertically or horizontally adjacent cells which both exceed the average number of events per cell for a particular type.

This embodiment may also comprise a neural network, a method for dynamically clearing selected portions of a running yarn to achieve a specific grade of yarn, and a method for simulating the effect of clearing a portion of the yarn sample.

Each of the embodiments may further include displaying electronically one or more of the cells including flaws and/or patterns in which the events may be displayed using different shades or colors to represent each different threshold or type of event.

This invention contemplates evaluation of any measurable yarn quality, and use of such measurements for the stated objectives. Such measurable qualities include, but are not limited to, diameter and its average, coefficient of variation and standard deviation, evenness, hairiness, the ratio of core-to-hair thickness, twist, color, neps, and thick and thin areas. Also, this invention contemplates electronically arranging the measured values side-by-side in the manner of a tapered yarn board (without displaying such) so that the event patterns at different frequencies of occurrence can be detected, and cleared, if desired.

BRIEF DESCRIPTION OF THE DRAWINGS

Other objects, features and advantages will occur to those skilled in the art from the following description of a preferred embodiment and the accompanying drawings in which.

DESCRIPTION OF THE PREFERRED EMBODIMENT

This invention for evaluating yarn or fabric samples may be accomplished by a method which may include electronically assigning one or more physical thresholds for each measured yarn quality; establishing an event when a measured yarn quality violates the physical threshold; delineating the yarn or fabric sample into one or more blocks or cells; locating the spatial position of one or more events in each delineated cell; sorting events in each cell into types of events; counting the number of each type of event in each cell wherein a type represents one or more assigned thresholds; comparing one or more of these cells to one or more of each other or to one or more reference cells; and evaluating the numerical and/or spatial relationship of the events in any one of the delineated cells to another delineated cell or reference cell. The invention may further include electronically grading and/or clearing a running yarn based on the outcome of the evaluation step.

The invention would not require a visible display or printout of the delineated cells, although the invention is intended to include such an embodiment. The invention could be accomplished by programming a computer so that types, locations, and sizes of faults or events that result in a particular grade are known. The computer could include a neural network programmed to weigh events properly, and combine such weights properly, to simulate human judgment used in manual grading. The neural network would originally be input with information from expert human inspectors regarding the relative importance of each particular event and of patterns of events in determining yarn grade.

As taught in copending application Ser. No. 08/603,587 which is incorporated herein by reference, the method preferably utilizes qualities such as yarn diameter measured at a large number of closely spaced locations along a length of yarn. This may be accomplished with an electronic sensor such as a linear CCD array and a light source for shining a light into a measurement zone through which the yarn is moved. The CCD captures a shadow image of the yarn. This data is electronically processed to calculate and define each measurement from this shadow image. This invention envisions any number of other imaging means for compiling or gathering data measurements for use with the software including but not limited to capacitance measurers; video cameras; electronic scanning devices; fiber optic sensors and imaging devices; and other sensors of backscattered particles, X-rays, or magnetic resonance.

These calculated measurements are then electronically compared to predetermined or assigned physical thresholds. These physical thresholds may represent one or more minimum or maximum quality characteristics a yarn must have to qualify for a particular grade of yarn. Physical thresholds may include virtually any parameter used to measure yarn qualities or characteristics. Qualities include but are not limited to maximum and minimum yarn diameter, length of a given event, ratio of core-to-hair thickness, length of a yarn twist, size and number of neps, color variations defined by predetermined shades or density of light received by the sensor, frequency of a given type of event, and evenness. Using the assigned thresholds as guidelines or boundaries, the software establishes a fault or "event" when a calculated measurement falls outside or inside the assigned maximum and/or minimum thresholds, respectively.

Figure 1:
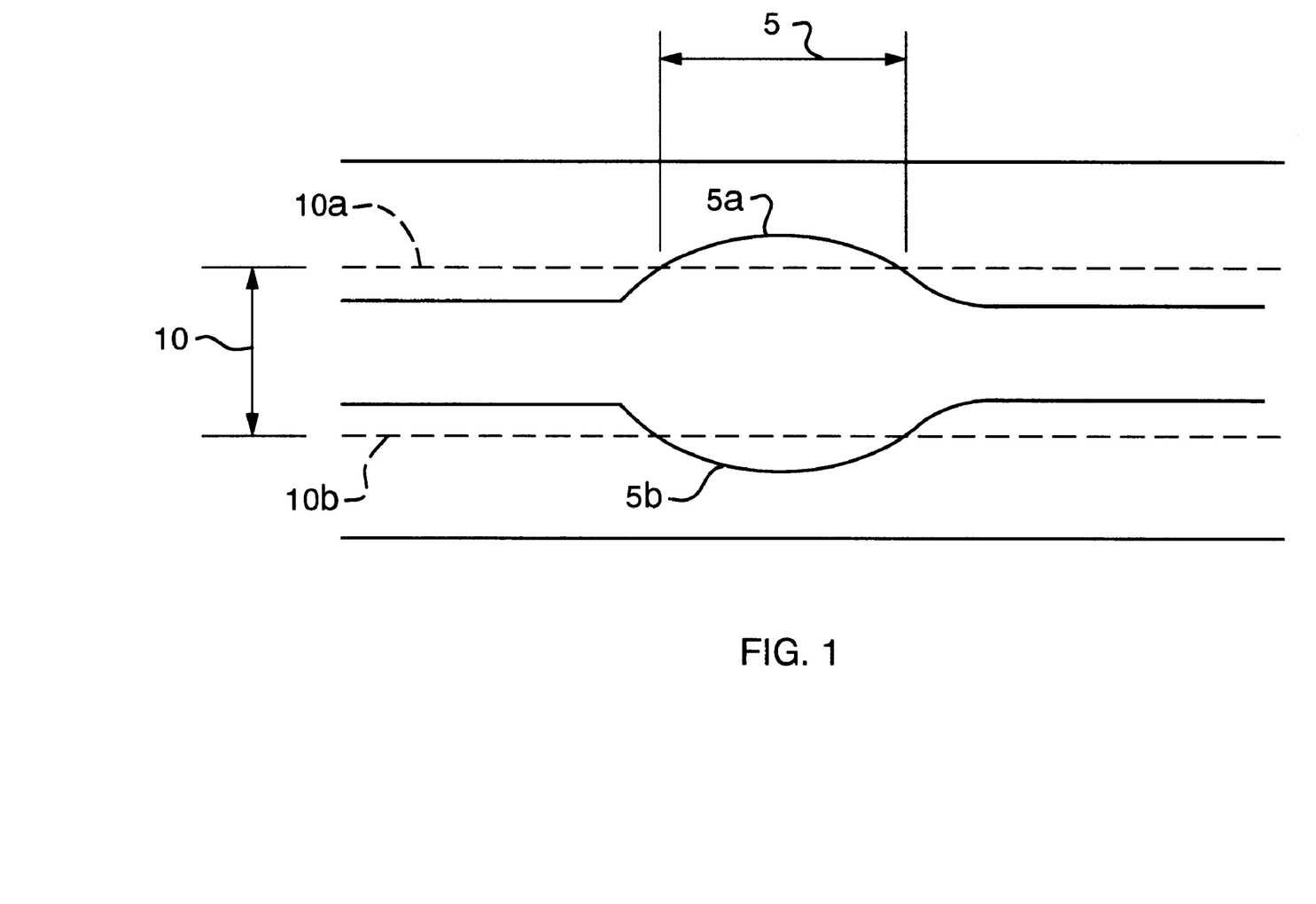
FIG. 1 is a view of an event which is evaluated by this invention.

For example, instances where the diameter of the yarn exceeds or is less than a preset maximum or minimum assigned threshold, respectively, are determined and recorded as "events". An example of one such event 5 is shown in FIG. 1. Lines 10A and 10B represent the maximum outer boundary of assigned diameter threshold 10. Event areas 5A and 5B show the area of yarn material which exceeds assigned diameter threshold 10. Alternatively, other yarn qualities or quality variations, such as coefficient of variation and standard deviation, evenness, hairiness, the ratio of core-to-hair thickness, twist, color, neps, and thick and thin areas, may be similarly compared and recorded as events.

This invention includes sorting events into "types" of events. A type of event may include one or more assigned thresholds. For example, one type may consist of all events which represent yarn faults which are greater than 0.25 inches in diameter and are between 0.25 inches and 0.50 inches long.

Types, quantity, location, and patterns of events all contribute to determining yarn quality. Concentrated numbers of events and patterns can be determined by electronically delineating a measured yarn or fabric sample into blocks or cells that are portions of the whole, or possibly the entire, data set. Quantities of events can be counted and their locations determined and compared cell-by-cell.

The comparison step, which may be used to find an unacceptable concentration of events, may include calculating an average number of events per cell for each type; determining if the number of events of each type occurring within each cell exceeds the average number of events per cell for each type; and locating two or more vertically or horizontally adjacent cells which both exceed the average number of events per cell for a particular type.

The comparison step may also be used to locate non-linear patterns of events by defining the location of events within a cell and comparing these locations with the location of events in other cells of a given yarn or fabric sample. A potentially unacceptable pattern may be found where two or more cells contain events at the same or similar locations within their respective cell. Whether or not the software will find a pattern unacceptable will depend on previously input guidelines which may include but are not limited to proximity of similar cells to one another and randomness of the similar cells' location within a given sample.

Figure 2:
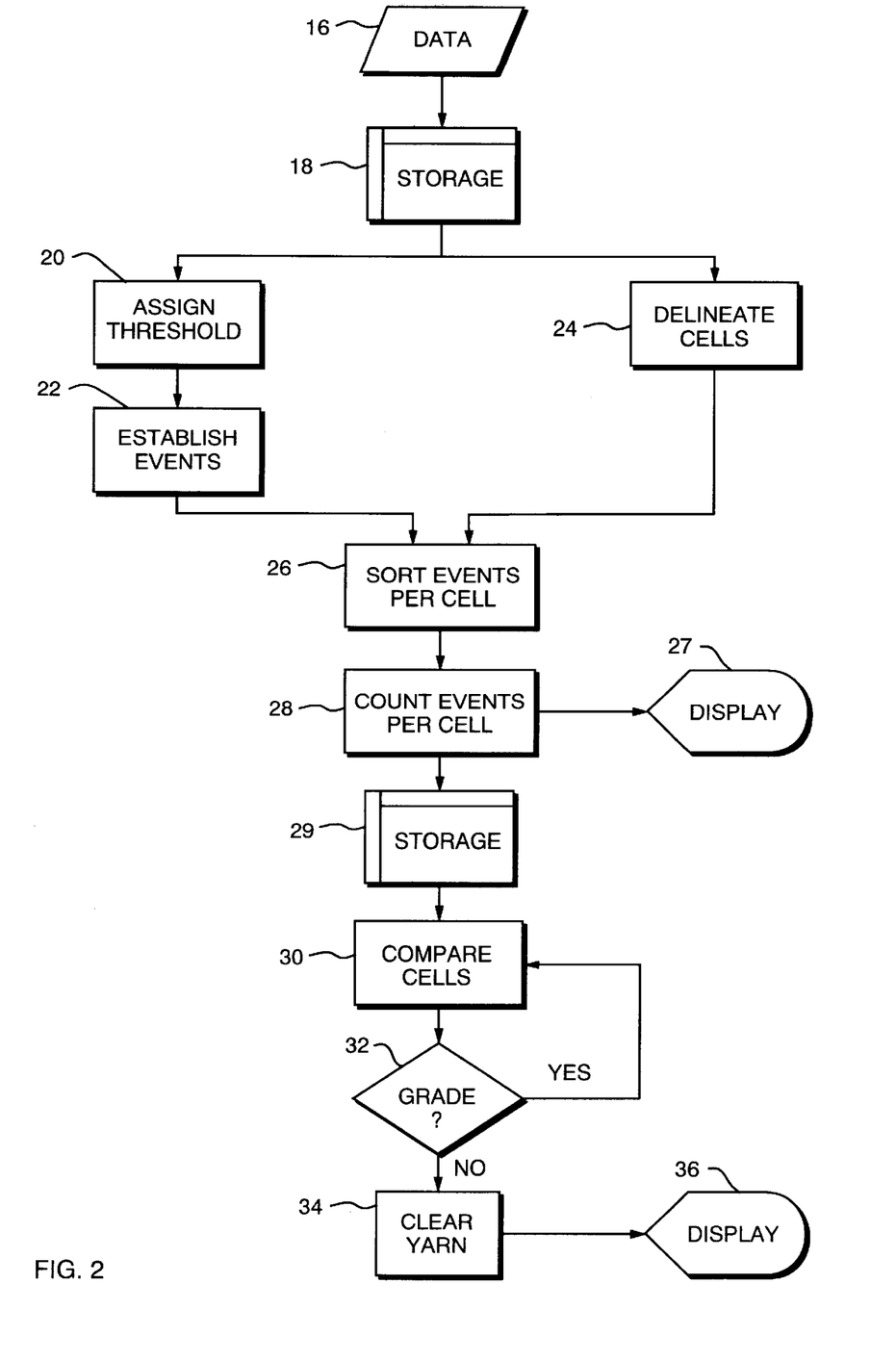
FIG. 2 is a schematic diagram of a preferred embodiment of this invention.

A preferred embodiment of this invention, shown in FIG. 2, features software for electronically evaluating one or more measured qualities of one or more yarn or fabric samples. Data from a sensing source illustrated by Data Box 16 is communicated to internal storage 18 and then processed using software which utilizes the following steps.

One or more physical thresholds are assigned for each measured yarn quality in assigning step 20. The physical thresholds could be input into the computer manually for each evaluation or could be a set group of thresholds previously input into the computer to represent parameters necessary for a particular grade. In the latter instance, a person could merely assign a grade of yarn desired and the computer would assign the corresponding thresholds for that grade. The software could also establish a maximum possible grade for a running yarn based on predetermined cost and material considerations, and then assign corresponding thresholds for that grade.

Figure 5:
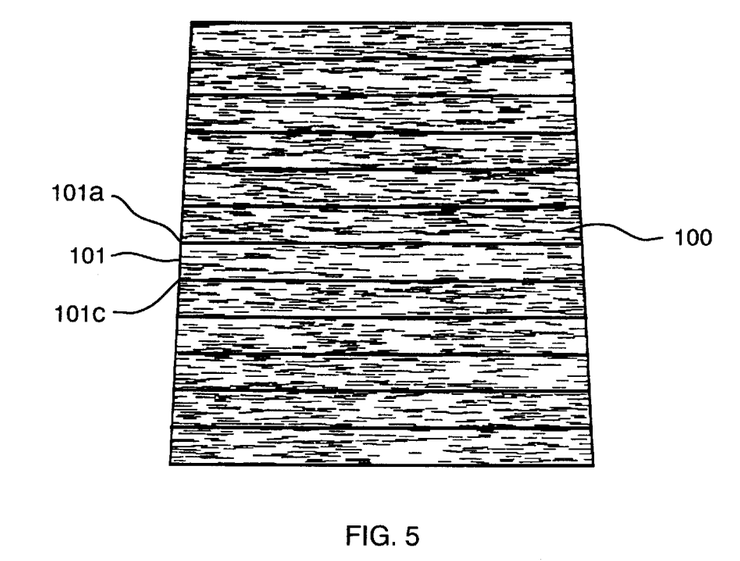
FIGS. 5 and 5A are views of a displayed cell of this invention.
Figure 5A:
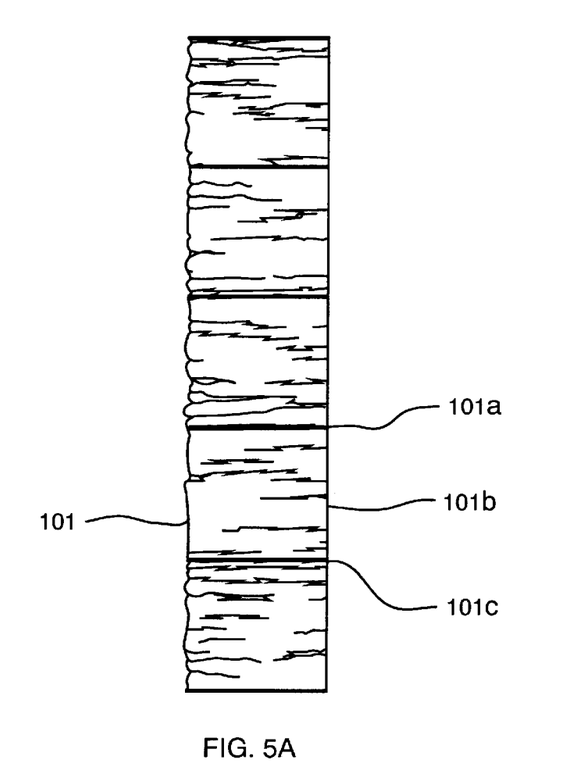
Figure 6:
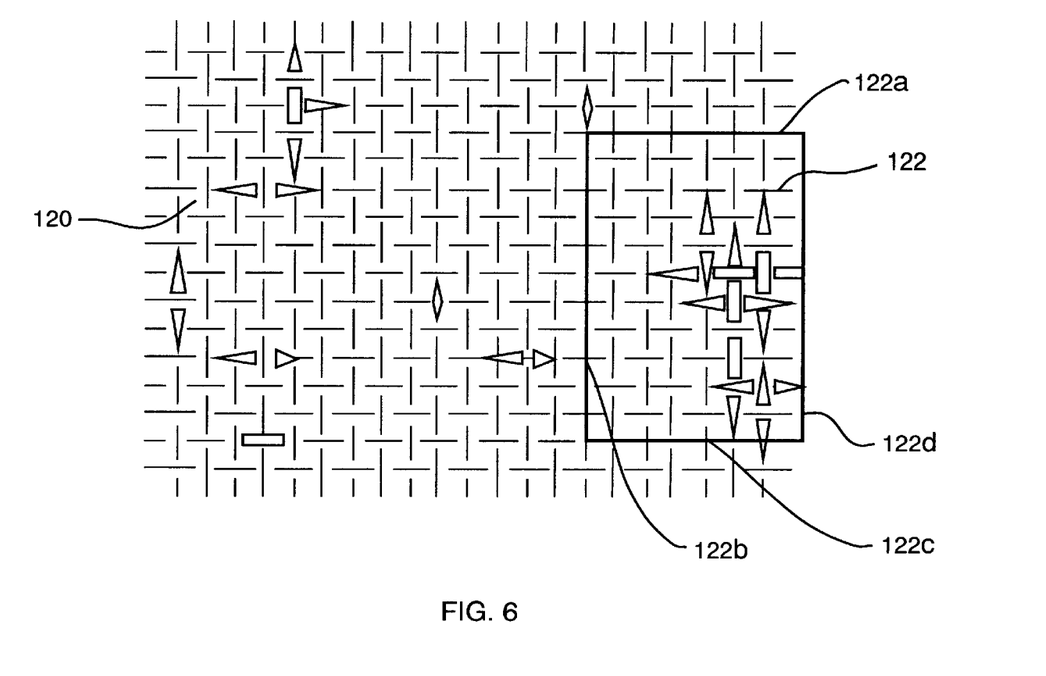
FIGS. 6 and 6A are alternate views of a displayed cell of this invention.

After assignment of thresholds, the software, in establishing step 22, using the calculated measurements, establishes that an event exists when a calculated measurement of a measured yarn quality violates or exceeds an assigned threshold. Either before, contemporaneous with, or after the events are established, the calculated measurements are also used to delineate one or more cells in delineating step 24, wherein each cell represents one or more portions of the yarn or fabric sample as shown in FIG. 5 or 6.

Using both the established events from step 22 and the delineated cells from step 24, the events in each cell are sorted into types of events in sorting step 26, wherein a type is defined by one or more physical thresholds which are different in scope from another type. After sorting the events into types per cell, the number of events of each type which occur within each cell are counted in counting step 28.

The preferred embodiment only stores the data from delineating step 24 and counting step 28 for further use with the software. The preferred embodiment does not continue to store the data originally introduced from Data Box 16. In storing step 29 the data from delineating step 24 and counting step 28 is internally stored in an attached computer's memory.

The type and number of each type of events in each cell are compared in comparing step 30 with a reference cell to determine whether the number of events of each type in each cell exceeds a predetermined number of events of the same type of events in the reference cell. The reference cell may consist of a hypothetical cell based on an average number of measured events established in each cell for all cells measured for a given sample. The reference cell may also consist of a previously measured and stored cell which represents the standard for a particular grade of yarn. In sum, the reference cell could be any cell that might serve as a base or template to which the evaluated cell could be compared. The cells including events may be displayed using various shades and colors as in display step 27 and in FIGS. 5, 5A, 6, and 6A.

The preferred embodiment may further comprise a neural network step 32 which simulates human judgment used to manually grade yarn or fabric. The neural network may also be used to dynamically clear selected portions of a running yarn or fabric on-line, as in step 34, to upgrade the running yarn by instructing a downstream yarn clearer to remove selected portion of the yarn on-line based on the results of the evaluation step. This embodiment may further include a means for simulating and displaying the effect of clearing a selected portion of the yarn sample as in ancillary display step 36.

Figure 7:
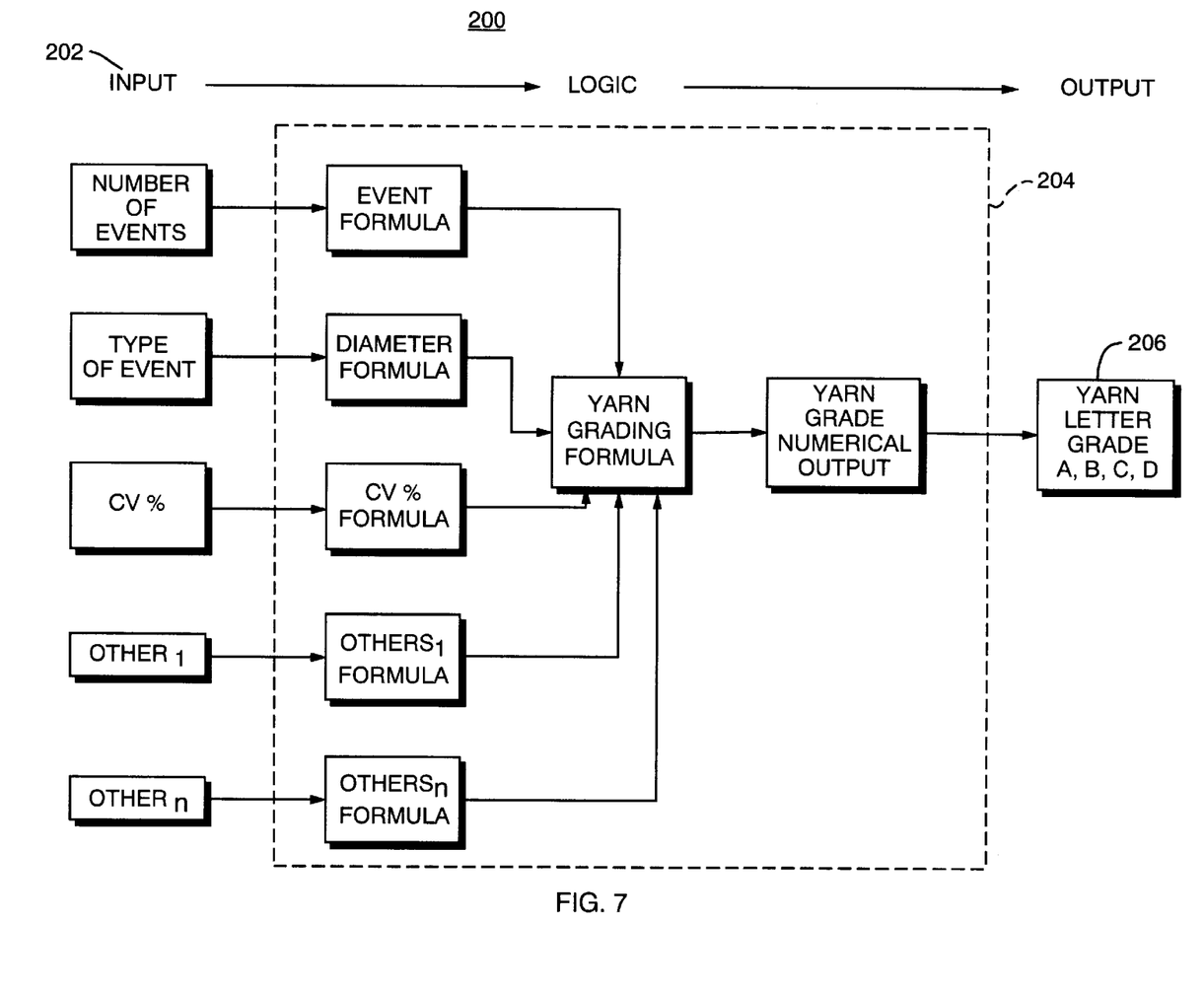
FIG. 7 is a schematic diagram of a neural network of this invention.

An example of such a neural network to determine the overall grade or quality of a yarn sample is schematically depicted in FIG. 7. The data resulting from the comparison of cells step 30 is introduced into the neural network as shown in column 202; including the number of one or more types of events, the average measurement for each quality measured, and the coefficient of variation for a given measured quality. These data measurements are further manipulated using predetermined formula's to calculate their respective weight. The formulas would previously have been input into the computer and would reflect the thought processes of human graders. The results of these formulas would be introduced into neural network logic 204 to produce an output 206 in the form of a letter grade based on quality for the measured yarn. Input column 202 provides for additional input data as needed for grading purposes.

The neural network could incorporate various measurements and calculations into its evaluation or grading system including but not limited to length of events, width of events, spatial relationship of events, types of events, color and shade of events, and moire effects from unwanted patterning.

Figure 3:
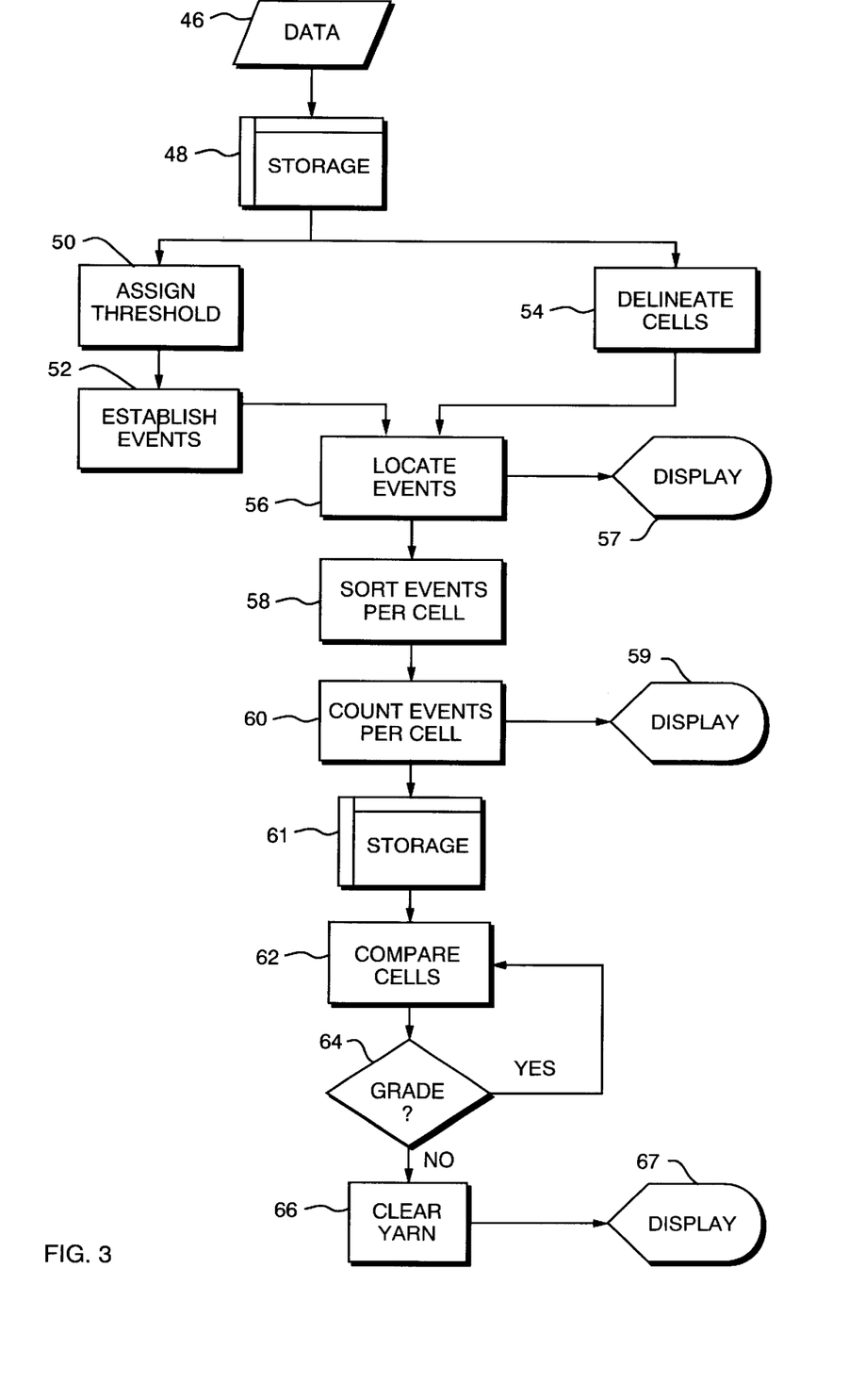
FIG. 3 is a schematic diagram of a preferred embodiment of this invention.

In a second preferred embodiment, shown in FIG. 3, this invention features software using an alternative method for electronically evaluating one or more measured qualities of one or more yarn or fabric samples. Data from a sensing source shown in Data Box 46 is communicated to internal storage 48 and is processed using software which utilizes the following steps which flow in a manner similar to that of the first embodiment described above: assigning step 50 in which a physical threshold for each measured yarn quality is assigned; establishing step 52 in which an event is established when the yarn quality violates the physical threshold; and delineating step 54 in which one or more cells is established, wherein each cell represents a portion of the yarn or fabric sample.

The second preferred embodiment of the software also utilizes locating step 56 in which the spatial location of each event in each cell is established. This could be accomplished by any number of ways used to describe or define the location of a point or points on a two-dimensional viewing area.

Similar to the first embodiment, the second embodiment of the software utilizes a sorting step 58 in which the events in each cell are sorted into types of events, wherein a type may include one or more physical thresholds; and a counting step 60 in which the number of events of each type which occur within each cell are counted. The data from locating step 56 and counting step 60 is internally stored in an attached computer's memory in storing step 61.

Comparing step 62 compares both the location and number of events types in one or more cells. The locations of events in one or more cells are compared to the locations of events in one or more of the other cells in the yarn or fabric sample to determine whether a non-linear pattern of events, or moire, exists between two or more cells within a yarn or fabric sample. The type and number of each type of events in one or more cells are also compared with a reference cell to determine whether the number of events of each type in each cell exceeds a predetermined number of events of the same type of events in the reference cell. The cells, including events, may be displayed using various shades and colors as in display steps 57 and 59.

The second embodiment may further comprise a neural network step 64 which simulates human judgment used to manually grade yarn and which may dynamically clear selected portions of a running yarn on-line to upgrade the running yarn as in dynamically clearing step 66. The second embodiment may further include a means for simulating and displaying the effect of clearing a selected portion of the yarn sample as in ancillary display step 67.

Figure 4:
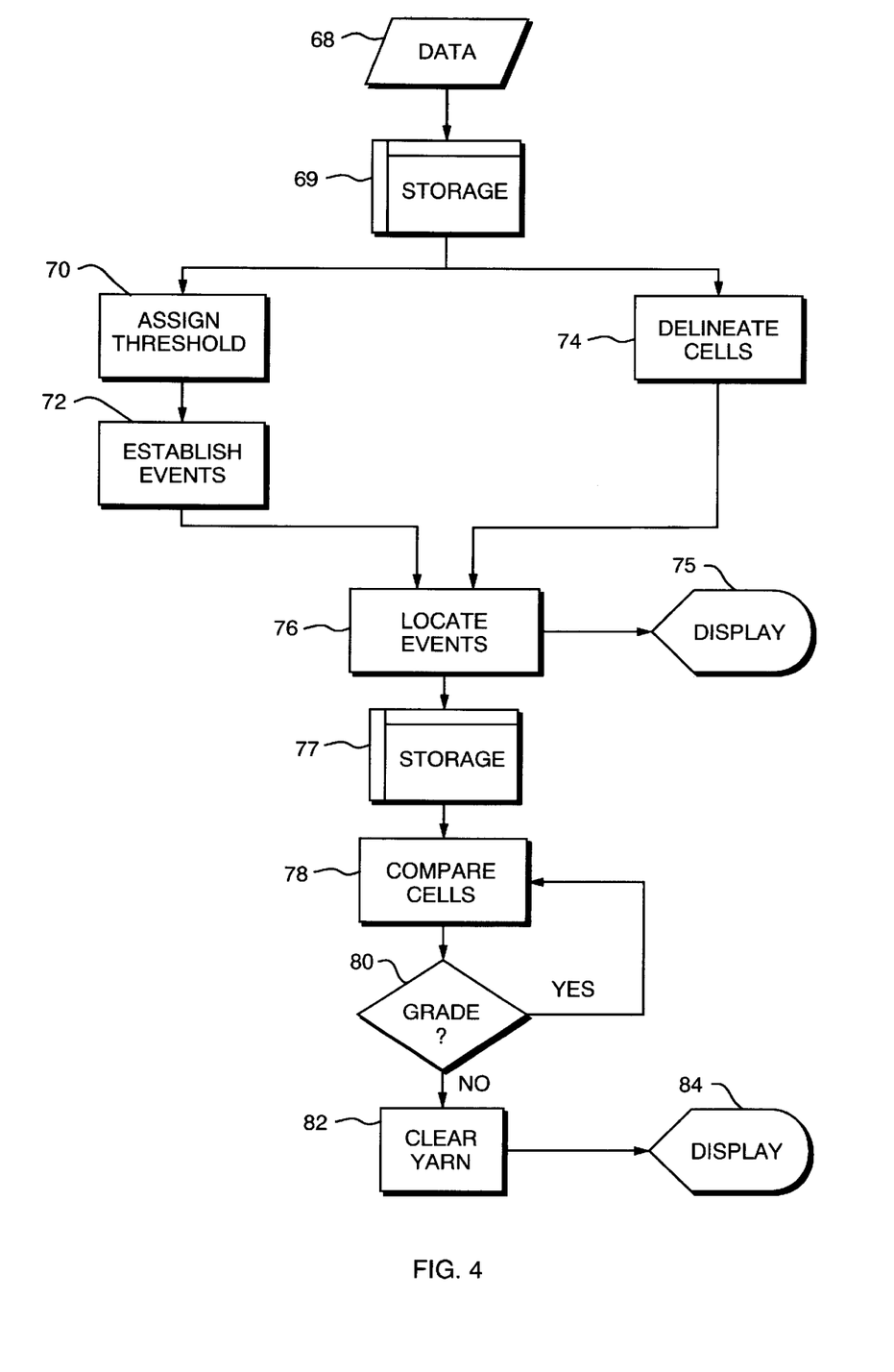
FIG. 4 is a schematic diagram of a preferred embodiment of this invention.

A third preferred embodiment, shown in FIG. 4, features software using another alternate method for electronically evaluating one or more measured qualities of one or more yarn samples. Data from a sensing source shown in Data Box 68 is processed using software which utilizes the following steps which flow in a manner similar to that of the first and second embodiments described above: assigning step 70 in which a physical threshold for each measured yarn quality is assigned; establishing step 72 in which an event is established when the yarn quality violates the physical threshold; delineating step 74 in which one or more cells is established, wherein each cell represents a portion of the yarn or fabric sample; locating step 76 in which the location of each event in each cell is memorized; comparing step 78 in which the location of events in each cell is compared to the location of events in all the other cells in the yarn or fabric sample to determine whether a pattern of events exists between two or more cells within a yarn or fabric sample; and grading step 80. As with the first two embodiments, the third embodiment may also include a neural network step 80 and dynamically clearing step 82.

Figure 6A:
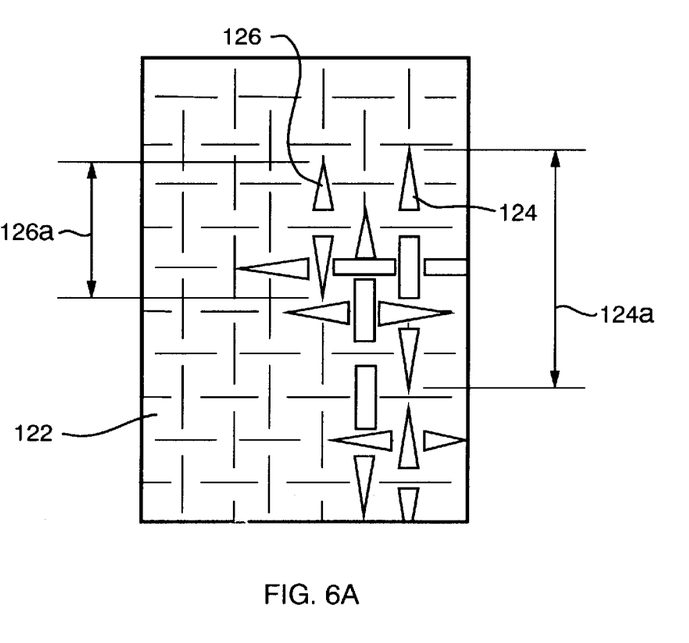

Each of the above embodiments may further include displaying electronically one or more of the cells including flaws and/or patterns. FIG. 5 is an example of an electronic display of a simulated taper board 100 partially delineated into cells, for example cell 101. Cell 101 is defined by lines 101A and 101C shown in FIG. 5 and line 101B shown in FIG. 5A. FIG. 6 is an example of an electronic display of a simulated fabric 120 partially delineated into cells, for example cell 122 which is defined by lines 122A, 122B, 122C, and 122D. FIG. 6A is an enlarged view of cell 122 showing the different type of events, for example event 124, having a length shown by arrow 124A, represents an area of yarn which exceeded an assigned length threshold for a particular diameter threshold. For comparison, event 126, having a length shown by arrow 126A, is a different type of event because it represents an area of yarn which exceeded a shorter assigned length threshold than event 124 for a particular diameter threshold.

The comparison step, used to find an unacceptable concentration of events, may include calculating an average number of events per cell for each type; determining if the number of events of each type occurring within each cell exceeds the average number of events per cell for each type; and locating two or more vertically or horizontally adjacent cells which both exceed the average number of events per cell for a particular type.

The comparison step may also be used to locate non-linear patterns of events by defining the location of events within a cell and comparing these locations with the location of events in other cells of a given yarn or fabric sample. A potentially unacceptable pattern may be found where two or more cells contain events at the same or similar locations within their respective cells. Whether or not the software will find a pattern unacceptable will depend on previously input guidelines which may include but are not limited to proximity of similar cells to one another and randomness of the similar cells' location within a given sample.

It is envisioned that any number of yarn characteristics could be evaluated with this invention including diameter, length of diameter variations, coefficient of variation and standard deviation, evenness, hairiness, the ratio of core-to-hair thickness, twist, color, neps, and thick and thin areas.

Therefore, although specific features of the invention are shown in some drawings and not others, this is for convenience only as some feature may be combined with any or all of the other features in accordance with the invention.

Other embodiments will occur to those skilled in the art and are within the following claims.

What is claimed is:

1. A method for electronically evaluating one or more measured qualities of one or more yarn samples, comprising the steps of assigning one or more physical thresholds for each measured yarn quality;

establishing an event when a measured yarn quality violates the physical threshold;

establishing one or more cells, wherein each said cell represents one or more portions of the yarn sample configured as an electronic yarn board or fabric display;

sorting the events in each cell into types of events, wherein a type includes both a measured yarn quality and a physical threshold;

counting the number of events of each type which occur within one or more cells; and comparing the type and number of each type of events in each said cell with a reference cell to determine whether the number of events of each type in each cell exceeds a predetermined number of events of the same type of events in the reference cell.

2. The method of claim 1, further comprising dynamically clearing selected portions of a running yarn on-line.

3. The method of claim 1, wherein said physical threshold is a selected shade of gray from white to black.

4. The method of claim 1 further comprising displaying electronically said established cells including said events.

5. The method of claim 1, further comprising a neural network which simulates human judgment used to manually grade yarn.

6. The method of claim 5 wherein said neural network further comprises a means for dynamically clearing selected portions of a running yarn on-line to upgrade said running yarn.

7. The method of claim 6, further comprising simulating the effect of clearing a selected portion of said yarn sample.

8. The method of claim 1 comprising the steps of,
calculating an average number of events per cell for each type;
determining if the number of events of each type occurring within each cell exceed the average number of events per cell for each type; and
locating two or more vertically or horizontally adjacent cells which both exceed the average number of events per cell for a particular type.

9. A method for electronically evaluating one or more measured qualities of one or more yarn samples, comprising the steps of
assigning a physical threshold for each measured yarn quality;
establishing an event when the yarn quality violates the physical threshold;
establishing one or more cells, wherein each cell represents one or more portions of the yarn sample configured as an electronic yarn board or fabric display;
memorizing the location of each event in each cell; and
comparing the location of events in each cell to the location of events in one or more other cells in the yarn sample to determine whether a pattern of events exists between two or more cells within a yarn sample, of a running yarn on-line to upgrade said running yarn.

10. The method of claim 9, further comprising a means for dynamically clearing selected portions of a running yarn on-line.

11. The method of claim 9 wherein said physical threshold is a selected shade of gray between white and black.

12. The method of claim 9 further comprising displaying electronically said established cells including said events.

13. The method of claim 9, further comprising a neural network which simulates human judgment used to manually grade yarn.

14. The method of claim 9 wherein said neural network further comprises dynamically clearing selected portions of a running yarn on-line to upgrade said running yarn.

15. The method of claim 9, further comprises simulating the effect of clearing a selected portion of said yarn sample.

16. A method for electronically evaluating one or more measured qualities of one or more yarn samples, comprising the steps of
assigning one or more physical thresholds for each measured yarn quality;
establishing an event when a measured yarn quality violates the physical threshold;
establishing one or more cells, wherein each said cell represents one or more portions of the yarn sample configured as an electronic yarn board or fabric display;
sorting the events in each cell into types of events, wherein a type includes both a measured yarn quality and a physical threshold;
counting the number of events of each type which occur within each cell;
memorizing the location of each event in each cell;
comparing the type and number of each type of events in each said cell with a reference cell to determine whether the number of events of each type in each cell exceeds a predetermined number of events of the same type of events in the reference cell; and
comparing the location of events in each cell to the location of events in one or more other cells in the yarn sample to determine whether a pattern of events exists between two or more cells within a yarn sample.

17. The method of claim 16 wherein said physical threshold is a selected shade of gray between white and black.

18. The method of claim 16 further comprising displaying electronically said established cells including said events.

19. The method of claim 16, further comprising a neural network which simulates human judgment used to manually grade yarn.

20. A method for electronically evaluating one or more measured qualities of one or more fabric samples, comprising the steps of
assigning a physical threshold for each measured fabric quality;
establishing an event when the fabric quality violates the physical threshold;
establishing one or more cells, wherein each cell represents a portion of the fabric sample defined by one or more spatial locations on an electronically configured fabric;
memorizing the location of each event in each cell;
comparing the location of events in each cell to the location of events in all the other cells in the fabric sample to determine whether a pattern of events exists between two or more cells within a fabric sample of a running yarn on line to upgrade said running yarn.

21. The method of claim 20 further comprising the steps
sorting the events in each cell into types of events, wherein type includes both a measured fabric quality and a physical threshold;
counting the number of events of each type which occur within each cell;
calculating an average number of events per cell for each type;
determining if the number of events of each type occurring within each cell exceeds the average number of events per cell for each type; and
locating two or more vertically or horizontally adjacent cells which both exceed the average number of events per cell for a particular type.

22. The method of claim 20 wherein said physical threshold is a selected shade of gray between white and black.

23. The method of claim 20, further comprising a neural network which simulates human judgment used to manually grade fabric.

24. The method of claim 20 further comprising displaying electronically said established cells including said events.

* * * * *